(12) United States Patent
Da Silva et al.

(10) Patent No.: US 9,897,533 B2
(45) Date of Patent: Feb. 20, 2018

(54) STRUCTURAL HEALTH MONITORING SENSORY ARRANGEMENT INTEGRATED WITHIN A SELF-HEALING SYSTEM

(71) Applicant: Embraer S.A., Sao Jose dos Campos-SP (BR)

(72) Inventors: Paulo Anchieta Da Silva, Sao Jose dos Campos (BR); Fernando Dotta, Sao Jose dos Campos (BR); Ricardo Pinheiro Rulli, Sao Jose dos Campos (BR)

(73) Assignee: Embraer S.A., São José dos Campos (BR)

(*) Notice: Subject to any disclaimer, the term of this patent is extended or adjusted under 35 U.S.C. 154(b) by 304 days.

(21) Appl. No.: 14/309,484

(22) Filed: Jun. 19, 2014

(65) Prior Publication Data

US 2015/0369723 A1 Dec. 24, 2015

(51) Int. Cl.

| | |
|---|---|
| *G01N 21/17* | (2006.01) |
| *G01N 29/09* | (2006.01) |
| *G01N 27/02* | (2006.01) |
| *B05C 9/10* | (2006.01) |
| *B05C 11/10* | (2006.01) |
| *B05D 5/00* | (2006.01) |
| *G01N 29/04* | (2006.01) |
| *G01N 29/34* | (2006.01) |

(Continued)

(52) U.S. Cl.
CPC ............... *G01N 21/17* (2013.01); *B05C 9/10* (2013.01); *B05C 11/1015* (2013.01); *B05D 5/005* (2013.01); *B29C 73/22* (2013.01); *G01N 27/02* (2013.01); *G01N 29/043* (2013.01); *G01N 29/09* (2013.01); *G01N 29/348* (2013.01); *G06Q 50/22* (2013.01); *G01N 2291/0258* (2013.01); *G01N 2291/2694* (2013.01)

(58) Field of Classification Search
USPC ...... 118/669, 712, 506, 408; 73/629; 156/94
See application file for complete search history.

(56) References Cited

U.S. PATENT DOCUMENTS

| | | | |
|---|---|---|---|
| 6,518,330 B2 * | 2/2003 | White | B29C 73/163 428/402.21 |
| 2010/0119704 A1 | 5/2010 | Hemmelgarn et al. | |
| 2011/0023611 A1 | 2/2011 | Jones et al. | |

OTHER PUBLICATIONS

Murphy, Erin B., et al., "The world of smart healable materials," Progress in Polymer Science, vol. 35, No. 1-2, 2010, pp. 223-251, XP026852569.

(Continued)

*Primary Examiner* — Yewebdar T Tadesse
(74) *Attorney, Agent, or Firm* — Nixon & Vanderhye P.C.

(57) ABSTRACT

An integrated system and method to acquire the health state of a structure identifying the presence of damage, and to self-repair the damage in the considered structure. A sensor network installed in the structure is interrogated by a dedicated hardware for damage detection. In case of damage is detected by the sensor network in the structure, the sensor network is triggered and generates harmonic excitation in the structure. Due to the excitation, the natural frequency of vascular microtubes and/or capsules presented in the structure is reached, promoting their disruption. The vascular microtubes and/or capsules disruption along the damage releases the healing compound, repairing the damaged portion of the structure.

17 Claims, 5 Drawing Sheets

Example of the structural integrity management system evaluation and healing process

(51) Int. Cl.
*B29C 73/22* (2006.01)
*G06Q 50/22* (2018.01)

(56) References Cited

OTHER PUBLICATIONS

International Search Report and Written Opinion of the International Searching Authority dated Oct. 16, 2015, issued in corresponding International Application No. PCT/BR2015/000084.

* cited by examiner

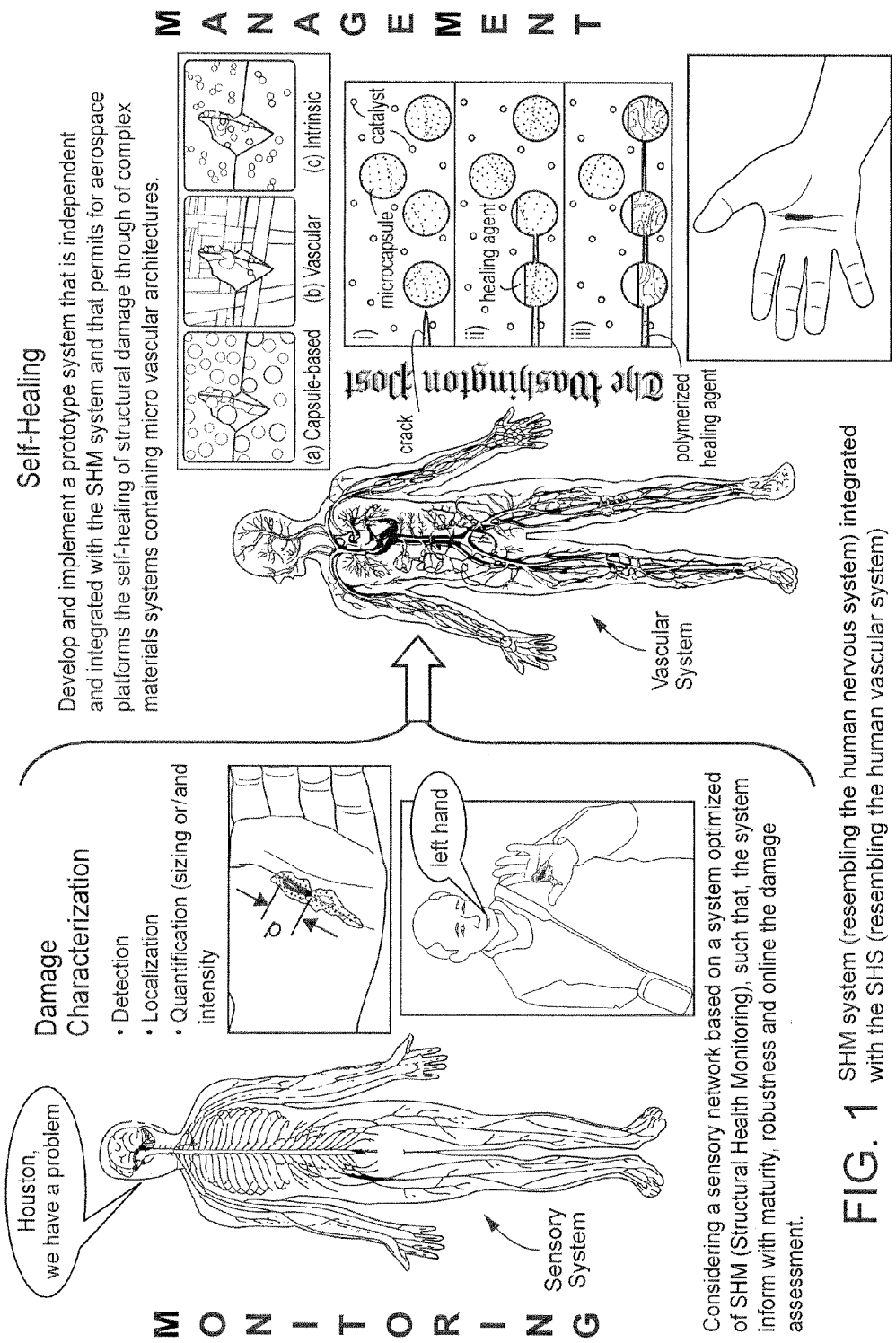
FIG. 1 SHM system (resembling the human nervous system) integrated with the SHS (resembling the human vascular system)

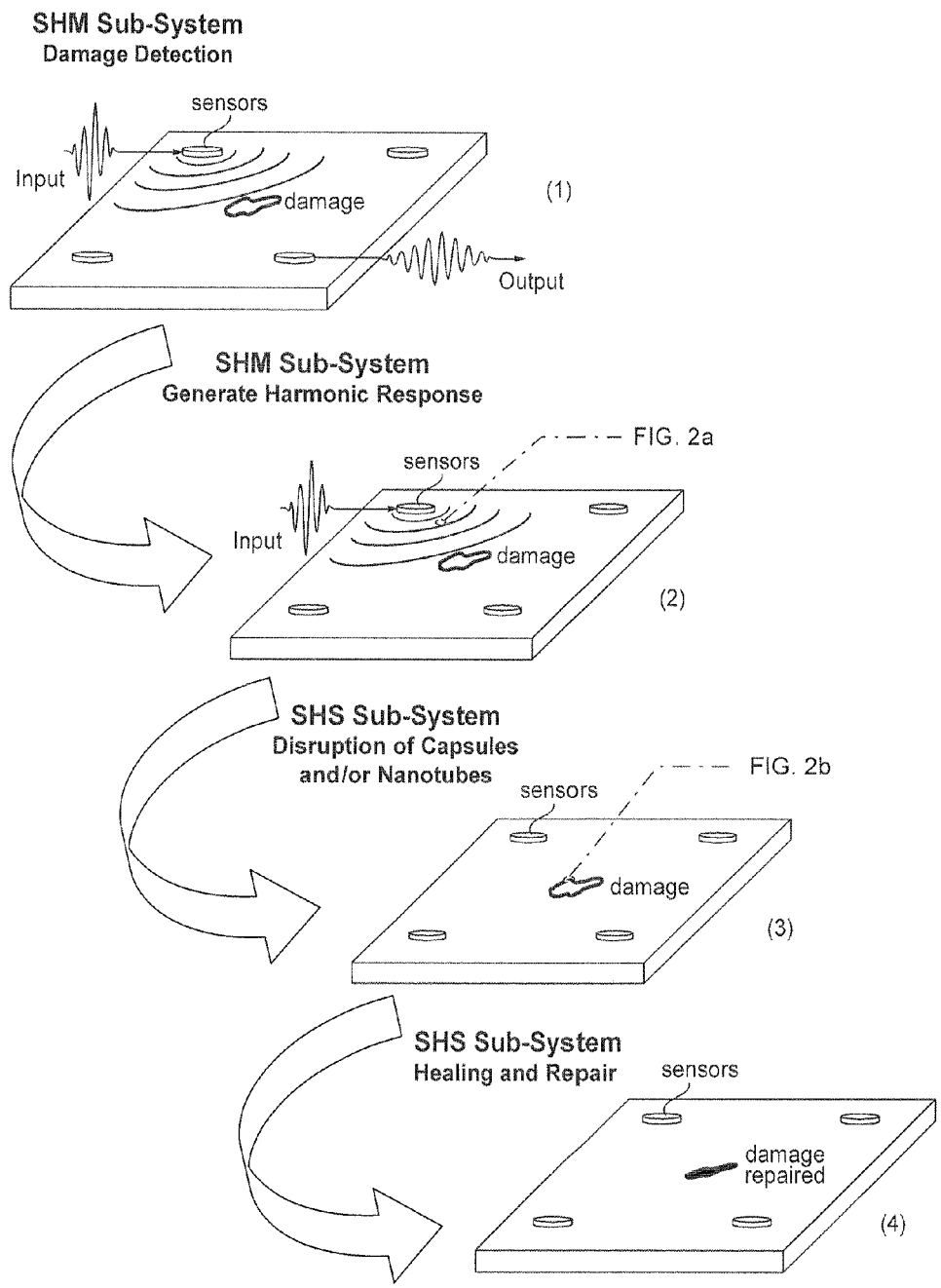
FIG. 2  Damage detection and healing by SHM sub-system integrated with SHS sub-system Example of the structural integrity management system evaluation and healing process

STRUCTURAL HEALTH MONITORING SENSORY ARRANGEMENT INTEGRATED WITHIN A SELF-HEALING SYSTEM

CROSS-REFERENCE TO RELATED APPLICATIONS

None.

STATEMENT REGARDING FEDERALLY SPONSORED RESEARCH OR DEVELOPMENT

None.

FIELD

The technologies herein relate to structural health monitoring (herein called "SHM") including sensors systems that automatically detect damage to structures including but not limited to aircraft, and to such sensor systems related to smart materials with capabilities of performing self-healing ("SHS") in the structural damages detected.

BACKGROUND

The human body has an amazing ability to heal itself when hurt in certain ways. For example, when your body incurs a minor cut or scrape, various complex mechanisms activate that heal and repair the damage. Generally speaking, however, our machines are unable to do the same.

It is highly desirable to reduce maintenance costs by minimizing explicit preemptory maintenance and to prevent catastrophic failures. An ultimate goal is to monitor the integrity of the structure in operating conditions during its entire working life. The development of in-service structural health monitoring (SHM) and damage detection techniques has attracted a large number of academic and industrial researchers.

Once damage is detected during operation of the structural platform, in general, a management process is performed through damage identification to determine whether to continue operation or to stop operation in order to perform structural repair.

Different kinds of damage may occur due to severe operational conditions. For example, damage can be caused by fatigue, erosion, corrosion, impact, moisture and/or other effects. The operational life cycle of a structural platform can be significantly reduced. In some cases, the entire structural component must be replaced instead of being repaired.

Seeking safety improvement, reduction of maintenance cost and human error, efforts are underway to develop automatic SHM systems capable of inspecting and detecting damages in real time without need for human interference or attention. Therefore, new SHM technologies will lead to early detection of damage that often in the past was identified only through scheduled manual inspections.

In general, "self-healing material" defines those materials that in the presence of damage can self-repair spontaneously or with the aid of a stimulus, and thus maintain its functionality or otherwise continue to function. The literature shows that different strategies and approaches have been investigated to provide this feature in all classes of materials including for example polymers, metals and ceramics.

The concept of self-healing of damage in materials is of great interest to the industry particularly in the following applications in structural platforms:

Structural components for which reliability, even in overload conditions, is of critical importance;
Surfaces where damages are not allowed, as in anti-corrosive coatings, decorative paints and thermal barrier coatings;
Structural components inaccessible or access difficult for inspections and repairs;
Structural components that require long life;
Other.

One useful strategy in self-healing polymers has been the incorporation of microcapsules or hollow glass fibers that, when broken, release a healing agent. Other mechanisms, such as the use of micro-vascular networks, have also been used. In the case of polymer matrix materials that have intrinsic self-healing, an external stimulus is required, e.g., heating is applied.

For self-healing metal, a primary focus in the past has been on the technologies of coatings applied to surfaces of metal alloys. Research conducted in scientific and technological bases on the subject of self-healing metal showed a low number of examples of application of this concept as compared to some other classes of materials.

For ceramic materials, although the typical self-healing process requires high temperature, the regeneration of properties at lower temperatures can be obtained if the grain boundary contains a vitreous phase. Such ceramic systems are able to surpass inherent problems of traditional ceramics, i.e., low fracture toughness, sensitivity to thermal shock, mechanical stiffness and low reliability.

BRIEF DESCRIPTION OF THE DRAWINGS

The following detailed description of exemplary non-limiting illustrative embodiments is to be read in conjunction with the drawings of which:

FIG. 1 shows an example non-limiting SHM system (in this case analogized to a system resembling the human nervous system) integrated with the SHS (in this case analogized to a system resembling the human vascular system);

FIG. 2 shows an example non-limiting damage detection and healing by SHM sub-system integrated with SHS sub-system;

DETAILED DESCRIPTION

In an example non-limiting embodiment, system and method for damage detection for structural platforms using structural health monitoring is integrated to a system and method capable of repairing the damage in the structure considering a self-healing system.

Using a sensory network based on a Structural Health Monitoring (SHM) system, the system informs a damage assessment with maturity and robustness.

An output of the SHM system is the damage characterization, which can be based on:

Detection;
Localization; and/or
Quantification (sizing or/and load intensity).

After knowing about the characterization of the damage, a Self-Healing System (SHS) that may be independent is integrated to the SHM system. The integrated SHS to SHM arrangement allows self-healing of damage in the structure through the use of smart materials systems containing micro vascular architecture and/or micro capsular architectures.

Like the human nervous system shown in FIG. 1, the example non-limiting SHM system senses the presence of damage. Also like the human vascular system, the non-limiting SHS performs self-healing of the damage. In this approach, these systems are independent but integrated, exchanging information (see FIG. 1).

In more detail, referring to FIG. 1, the SHM senses that there is a problem ("Houston, we have a problem"). Such an optimized SHM can provide a sensory network that can inform of damage based on maturity, robustness and/or online damage assessment. Such an SHM is integrated with an SHS system, which can be independent of the SHM and permit aerospace or other platforms to provide self-healing of structural damage through complex materials systems containing microvascular architectures. Such self-healing can be capsule-based, vascular based, intrinsic, e.g., through use of a polymer healing agent (using microcapsules and catalyst to provide self-healing of cracks or other structural damage for example). This is similar to how the human body characterizes damage by detection, localizes and quantifies damage (e.g., by sizing and/or intensity) such as detecting injury of the hand and then self-heal.

Figure 2A:
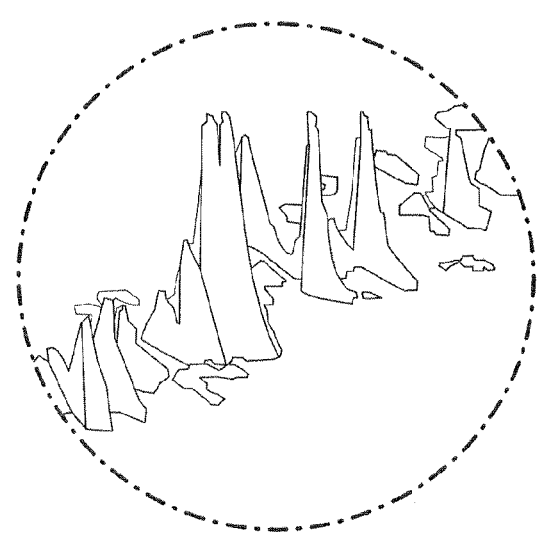
FIGS. 2A and 2B show more detailed breakouts of FIG. 2.

Therefore, example non-limiting embodiments provide a structural integrity management system providing the integration of a SHM sub-system that continually or continuously evaluates a structural platform. When the system detects damage, the system starts to generate excitation (mechanical, electrical, thermal, etc.) in the region nearby the damage, thereby triggering the self-healing system. In this approach, excitation is applied to the structure creating harmonic response until achieving the natural frequency of vascular microtubes and/or capsules that belong to the SHS sub-system (see FIG. 2(1)). Such harmonic response in one example implementation causes resonance or other constructive interference (see FIG. 2a). This harmonic response disrupts vascular microtubes and/or capsules (see FIG. 2(b)) so that they perform self-healing and repair structural damage in the damaged region (see FIG. 2(3), 2(4)).

Figure 2B:
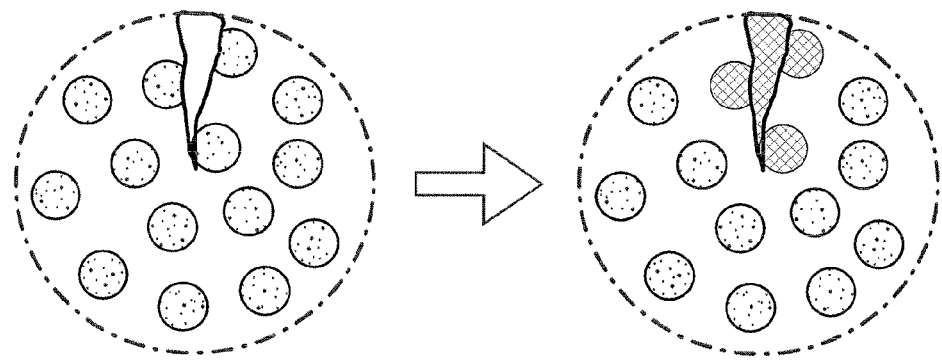

For example, as shown in FIG. 2(b), micro-tubes disposed in an area subjected to a constructively-interfering vibrational wave pattern can self-heal. For example, in one non-limiting example, a micro-encapsulated healing agent is embedded in a structural composite matrix containing a catalyst capable of polymerizing the healing agent. In this example embodiment, the harmonic response selectively induces cracks in the matrix. Different vibrational patterns can induce cracks or other disturbances in different areas. The cracks or other disturbances induced by the harmonic response rupture the microcapsules in the area of the cracks, releasing the healing agent into the crack plane through capillary action. The released healing agent contacts the catalyst, triggering polymerization that bonds the crack faces closed. See e.g., Martinez-Lucci et al., Self Healing in Metal Castings (American Foundry Association, 2011), incorporated herein by reference.

Figure 3:
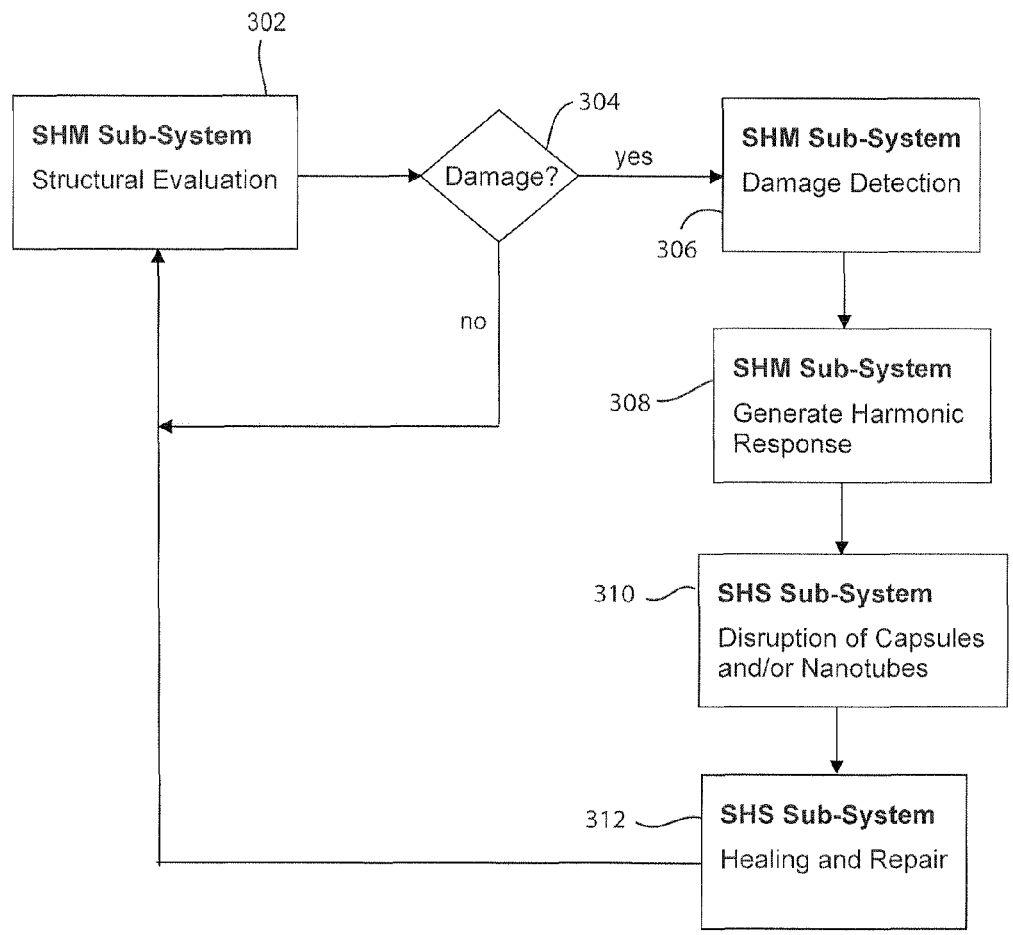
FIG. 3 shows an example non-limiting process for structural integrity management evaluation and self-healing.
Figure 4A:
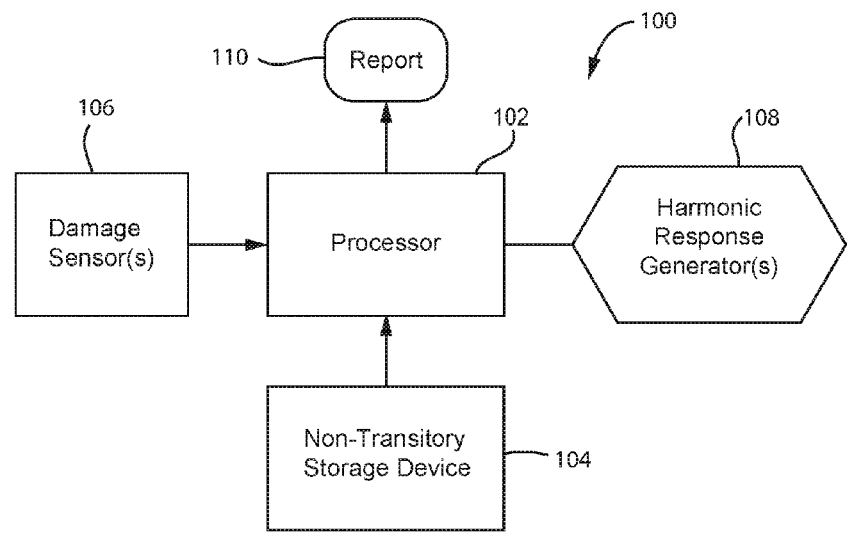
FIG. 4A shows an example non-limiting system for structural integrity management evaluation and self-healing.
Figure 4B:
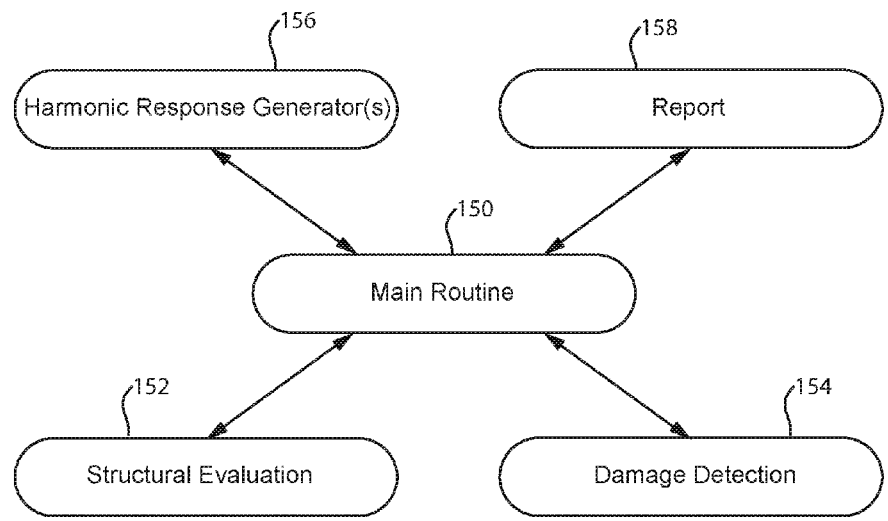
FIG. 4B shows an example non-limiting software structure.

FIG. 4A shows an example non-limiting system and FIG. 3 shows example non-limiting process steps. Referring to FIG. 4A, an example system 100 may include one or more computer processors 102 coupled to non-transitory storage 104 storing executable program instructions. For example, in one embodiment, processor 102 may comprise a microprocessor, gate array, computer processor, digital signal processor or other device that can perform a sequence of operations. In one example non-limiting embodiment, processor 102 executes a computer program comprising a sequence of program instructions (including a main routine 152 and one more subroutines 154, 156, 158 shown in FIG. 4B) stored in non-transitory storage device 104. In the example shown, the main routine software 150 executed by processor 102 calls a structural evaluation routine 152 that reads damage sensors 106 to perform structural evaluation 302. If no damage is detected ("no" exit to decision block 304), the main routine 150 can continually monitor the structure of interest until damage is detected ("yes" exit to decision block 304). Once such damage is detected, the main routine 150 calls a damage detection subroutine 154 to perform damage detection 306. Such damage detection can for example determine the precise extent, type and location of the damage, once again using one or more damage sensors 105. Damage sensors 106 can comprise any type of sensors such as optical, visual, machine vision, vibration testing, flex testing, strain gauges, temperature, deformation testing, audible or sound sensing, ultrasonic, infrared imaging, ultraviolet imaging, or any other type of sensing.

Once the precise location of the damage has been detected, main routine 150 can call the harmonic response generator excitation routine 156. Harmonic response generator excitation routine 156 operates in conjunction with harmonic response generator/exciter 106 to generate a harmonic response in the structure of interest. As one example, harmonic response generator 106 can comprise one or more vibrational transducers that generate vibration in a pattern and at a frequency and location that will disrupt capsules and/or nanotubes as described above to provide healing and repair (see block 308, 310, 312). The self-healing system may for example be accomplished as agents microencapsulated or microvascular networks or crosslinked thermo-reversible or adding an additive in thermoplastic thermofix matrix or elastomers with supramolecular structures with hydrogen bonds or molecular interdiffusion or repair photoinduced or living polymer.

One example non-limiting Structural Health Monitoring System (SHM) can comprise a plurality of transducers, including a plurality of pairs of actuators and sensors, a generator device to excite at least one of said sensors to produce ultrasonic guided waves, and a signal processor device to receive the signals reflected from damage identification. The example Self-Healing System (SHS) can comprise a self-healing material including a matrix of at least one polymer material, wherein a set of capsules are uniformly distributed and embedded in the matrix containing a liquid healing-agent, wherein the SHM system and the SHS system are integrated with a unique or distinct network of sensors/actuators. For example, the integrated system (SHM+SHS) can be exclusively one box control, or the integrated system (SHM+SHS) may be with box control separated for SHM and SHS. In one example non-limiting implementation, the sensors may comprise fiber optics sensors or piezoelectric sensors, and the structural health monitoring may comprise Lamb waves or electromechanical impedance or Fiber Bragg gratings or acoustic emission. In one example non-limiting implementation, the network sensors may be embedded in the structure or not embedded in the structure, and the generator device for the excitation may be mechanical, electrical and/or thermal.

Main routine 150 may then re-call structural evaluation subroutine 152 to re-evaluate the structure to determine whether it has been sufficiently healed and repaired to continue to be used. The process shown in FIG. 3 can be performed recursively until the structure is self-healed, or until main routine 150 determines that the structure cannot be self-healed and must instead be manually repaired or replaced (report generating subroutine 158). Thus, after healing, the SHM sub-system may also perform a reassessment of the structure certifying if the structure is safe for operation (see FIG. 3).

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A system for assessing the condition of and self-repairing a structural platform comprising:
    a Structural Health Monitoring System (SHM) comprising a plurality of transducers, including a plurality of pairs of actuators and sensors, a generator device to excite the at least one of said sensors to produce ultrasonic guided waves and a signal processor device to receive signals of damage detected in the structural platform;
    a Self-Healing System (SHS) comprising a self-healing material including a matrix of at least one polymer material, wherein a set of vascular microtubes or capsules are uniformly distributed and embedded in the matrix, the set of vascular microtubes or capsules containing a liquid healing-agent, the Self-Healing System is configured to create harmonic response achieving a natural frequency of the vascular microtubes or capsules thereby causing resonance or other constructive interference that disrupts the vascular microtubes or capsules so the vascular microtubes or capsules release the liquid agent to self-heal and repair detected structural damage in the damaged region; and
    wherein the SHM system and the SHS system are integrated with a unique or distinct network of the sensors and plurality of pairs of actuators, wherein:
    the integrated system (SHM+SHS) is exclusively one box control, or with box control separated for SHM and SHS.

2. The system according to claim 1, wherein the sensors comprise fiber optics sensors or piezoelectric sensors.

3. The system according to claim 1, wherein the structural health monitoring system uses electromechanical impedance or acoustic emission.

4. The system according to claim 1, wherein the network of the sensors and plurality of pairs of actuators is embedded in the structure.

5. The system according to claim 1, wherein the generator device for the excitation is a mechanical, electrical, and/or thermal generator.

6. The system according to claim 1, wherein the generator device for the excitation is the SHM system or the SHS system or another independent system.

7. The system according to claim 1, wherein the self-healing system comprises agents microencapsulated or microvascular networks or crosslinked thermo-reversible or adding an additive in thermoplastic thermofix matrix or elastomers with supramolecular structures with hydrogen bonds or molecular interdiffusion or repair photoinduced or living polymer.

8. The system according to claim 1, wherein the self-healing system comprises microencapsulated agents.

9. The system according to claim 1, wherein the self-healing system comprises microvascular networks.

10. The system according to claim 1, wherein the self-healing system comprises crosslinked thermo-reversible.

11. The system according to claim 1, wherein the self-healing system comprises thermoplastic thermofix matrix activatable by adding an additive.

12. The system according to claim 1, wherein the self-healing system comprises elastomers with supramolecular structures with hydrogen bonds.

13. The system according to claim 1, wherein the self-healing system comprises elastomers with supramolecular structures with molecular interdiffusion.

14. The system according to claim 1, wherein the self-healing system comprises elastomers with supramolecular structures with repair photoinduced polymer.

15. The system according to claim 1, wherein the self-healing system comprises elastomers with supramolecular structures with living polymer.

16. The system according to claim 1, wherein the network of the sensors and plurality of pairs of actuators is not embedded in the structure.

17. An integrated system for assessing the condition of and self-repairing a structural platform comprising:
    a plurality of actuators and sensors,
    at least one generator coupled to the plurality of actuators, the at least one generator exciting at least one of said plurality of actuators to produce ultrasonic guided waves,
    a signal processor coupled to the sensors, the signal processor is configured to process signals representing waves the sensors receive that are detected from damage in the structural platform to identify a damaged region;
    a self-healing material including a matrix of at least one polymer material and vascular microtubes or capsules distributed and embedded in the material, the vascular microtubes or capsules containing a liquid healing-agent,
    the signal processor is configured to control the at least one generator to selectively create harmonic response achieving a natural frequency of the vascular microtubes or capsules thereby causing resonance or other constructive interference that disrupts the vascular microtubes or capsules so the vascular microtubes or capsules release the liquid agent to self-heal and repair structural damage in the identified damaged region.

* * * * *